United States Patent [19]

Mita

[11] Patent Number: 5,143,784
[45] Date of Patent: Sep. 1, 1992

[54] SOLUBLE CALIXARENE DERIVATIVE AND FILMS THEREOF

[75] Inventor: Naoko Mita, Tokyo, Japan

[73] Assignee: NEC Corporation, Japan

[21] Appl. No.: 694,491

[22] Filed: May 2, 1991

[30] Foreign Application Priority Data

May 10, 1990 [JP] Japan .................................. 2-120310
Sep. 19, 1990 [JP] Japan .................................. 2-249151

[51] Int. Cl.$^5$ ........................ B32B 27/16; B05D 3/12; G03C 5/00; C08L 61/14
[52] U.S. Cl. ...................................... 428/336; 427/240; 430/296; 430/942; 430/967; 525/508; 528/129; 528/148
[58] Field of Search ............... 528/129, 137, 144, 147, 528/148, 142; 427/240; 428/336; 430/296, 942, 967; 525/508

[56] References Cited

U.S. PATENT DOCUMENTS 4,636,539 1/1987 Harris et al. ........................ 523/214

OTHER PUBLICATIONS

"Tetrahedron" vol. 39, No. 3, pp. 409–426, 1983.
*Calixarenes*, Gutsche, C. David, in "Monographs in Supramolecular Chemistry", Ed. J. F. Stoddart, Royal Society of Chemistry (1988).
Markowitz et al., J. Am. Chem. Soc., vol. 111 (1989), 8192-8200.
Gutsche et al., J. Am. Chem. Soc., vol. 107 (1985), 6059-6063.

*Primary Examiner*—John Kight, III
*Assistant Examiner*—Richard L. Jones
*Attorney, Agent, or Firm*—Leydig, Voit & Mayer

[57] ABSTRACT

A novel calixarene derivative, viz. acetylated methylcalix[n]arene (n is from 4 to 8), exhibits high solubilities in various organic solvents. A film of this compound can easily be formed by a conventional solution coating method such as spin coating, and the obtained film is hard and heat-resistant. A pattern of negative type can be formed in the obtained film by selectively irradiating the film with a high-energy ray such as ion beam, electron beam or X-ray to polymerize and insolubilize the irradiated regions and then removing the unirradiated region by dissolution in an organic solvent.

10 Claims, 2 Drawing Sheets

SOLUBLE CALIXARENE DERIVATIVE AND FILMS THEREOF

BACKGROUND OF THE INVENTION

This invention relates to a novel calixarene derivative which is soluble in organic solvents, films of the novel compound and a method of forming a pattern in a film formed by applying a solution of the novel compound to a substrate.

Calixarenes are cyclic oligomers formed by condensation of phenols and formaldehyde, and some calixarene derivatives can be obtained by substitution reactions after the condensation reaction.

Recent studies have revealed that calixarenes and their derivatives, like cyclodextrine and crown ethers, have the ability to form inclusion compounds. Synthesis of water soluble calixarenes has achieved a limited success, and it is under study to use calixarene derivatives as adsorbents for the recovery of, for example, uranyl ion from seawater or heavy metal ions from waste water.

There is good expectation that calixarenes and their derivatives will serve as advantageous functional materials. From a practical point of view, functional materials are generally required to be soluble in ordinary organic solvents and capable of providing films from solutions. However, known calixarenes and their derivatives are very low in solubilities in organic solvent, viz. below 1 wt %, and hence it is hardly conceivable to practically use these compounds in the form of films as functional materials. J. Am. Chem. Soc., Vol. 111 (1989), 8192–8200 shows to form very thin, monolayer-like films of some calixarene derivatives by using the Langmuir-Blodgett technique, but practical applications of such films will be quite limited.

SUMMARY OF THE INVENTION

It is an object of the present invention to provide a novel calixarene derivative which is high in solubilities in organic solvents and useful as a functional material.

It is another object of the invention to provide films of the novel calixarene derivative by using its solutions.

It is still another object of the invention to provide a method of forming a fine pattern in a film of the novel calixarene derivative.

We have succeeded in synthesizing a novel calixarene derivative, viz. acetylated methyl-calixarene, which is well soluble in various organic solvents and in forming heat-resistant films of this compound by a conventional spin coating method and, further, have discovered that a fine pattern can easily be formed in a spin-coated film of the novel compound by a conventional lithographic technique.

More definitely, the present invention provides acetylated methyl-calix[n]arene represented by the formula (I):

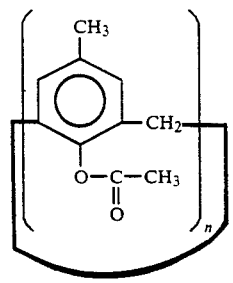

where n is an integer from 4 to 8.

The novel compound (I) is obtained by first forming methyl-calix[n]arene by reaction of p-methylphenol with formaldehyde in the presence of an alkali catalyst and then reacting methyl-calix[n]arene with, for example, acetic anhydride in the presence of an organic base.

The calixarene derivative (I) exhibits high solubilities in various organic solvents including widely used solvents such as, for example, pyridine, chloroform, dichloromethane, toluene, xylene and monochlorobenzene.

Initially we assumed that calixarenes with bulky alkyl groups would be soluble in organic solvents and tested octyl-calixarene, dodecyl-calixarene, etc., but the test results were negative. As a differnt measure for enhancing solubilities we have tried acetylation of lower alkyl-calixarenes and discovered that the acetylation of methyl-calixarene brings about surprising increases in solubilities in organic solvents and that, unexpectedly, high heat resistance of methyl-calixarene is not marred by acetylation.

With respect to acetylated methyl-calix[n]arene (I), the hexamer (n = 6) is particularly of interest because of exhibiting highest solubilities in various organic solvents.

In connection with the present invention we made studies on the acetylation of tert-butyl-calix[n]arene, which is already reported in J. Am. Chem. Soc., Vol. 107 (1985), 6059, and found that when n is 6 the acetylated calixarene exhibits high solubilities in organic solvents but is low in heat resistance and that when n is 4 or 8 the acetylated calixarene is very low in solubilities.

The present invention includes a film of the calixarene derivative (I). The film can be formed by applying a solution of the calixarene derivative (I) in an organic solvent to a substrate by a suitable method such as a spin coating method and drying or baking the coating film at a mildly elevated temperature. The solidified film is hard and very high in heat resistance and remains unchanged up to a temperature close to 400° C. By virtue of such high heat resistance in film form and good solubilities in organic solvents, the calixarene derivative (I) is useful as a functional material for various purposes.

An important merit of a heat-resistant film according to the invention is that the film can easily be removed, either entirely or selectively, by using an organic solvent since the film-forming process does not include any chemical reaction of the compound (I). In the case of conventional polyimide resins heat-resistant films are formed by chemical curing, and the cured films can hardly be removed by a dissolution method.

The present invention further provides a method of forming a pattern in a film of the calixarene derivative (I). The method comprises the steps of selectively irradiating the film with a high-energy ray thereby to polymerize and insolubilize selected regions of the film and thereafter removing the unirradiated regions of the film by dissolving in an organic solvent.

By this method it is possible to form a fine pattern of negative type with good rectangularity, and the obtained pattern is excellent in heat resistance.

Besides, we have discovered that even known calixarenes and calixarene derivatives, which are low in solubilities as mentioned hereinbefore, can be formed into films thicker than 10 nm by a spin coating method using low-concentration solutions.

DESCRIPTION OF THE PREFERRED EMBODIMENTS

Figure 1:
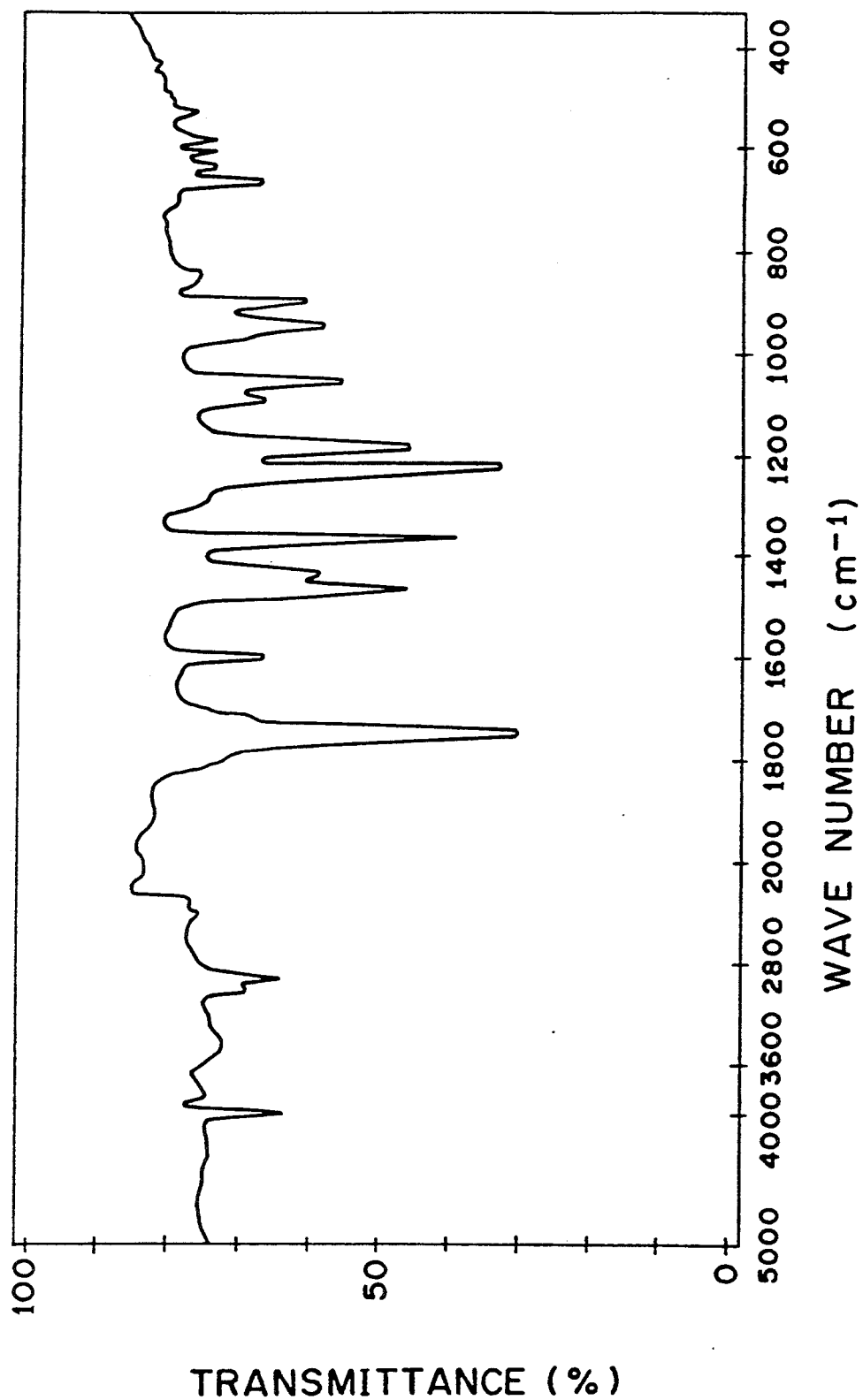
FIG. 1 is an infrared absorption spectrum chart of acetylated methyl-calix[6]arene.

In synthesizing acetylated methyl-calix[n]arene (I). the first step is the condensation reaction of p-methylphenol and formaldehyde or an aldehyde compound which gives formaldehyde, such as paraformaldehyde by way of example. The condensation reaction is carried out in a nonaqueous solvent such as, for example, benzene, toluene, xylene, heptane or dioxane in the presence of an alkali metal hydroxide such as hydroxide of Na, K, Rb, Cs or Fr. The quantity of the nonaqueous solvent is 5 to 30 parts by weight per 1 part by weight of p-methylphenol. For the reaction of 1 mol of p-methylphenol it is suitable to use 1.2–3.0 mols of formaldehyde, and the quantity of the alkali metal hydroxide is 0.05–0.5 mol % of the phenol. Preferably the alkali metal hydroxide is dissolved in water amounting to 0.1–1.0 wt % of the nonaqueous solvent in advance of the addition to the nonaqueous solvent. The reaction is carried out at a temperature ranging from 100° to 150° C., and preferably from 130° to 140° C., for 4 to 30 hr. After the reaction the precipitated product is separated from the solvent by filtration, washed with water and/or ethanol and dried preferably in vacuum at about 60° C.

Methyl-calix[n]arene (n is from 4 to 8) can be formed by the above one-stage process. It is most easy to form hexamer (n = 6). It is also possible to employ a multistage process to step-wise form the aimed oligoner one unit by one unit as is often employed for the preparation of other calix[n]arenes.

The next step is the acetylation of methylcalix[n]arene by reaction with an active derivative of acetic acid such as acetic anhydride or acetic acid chloride. The reaction is carried out in a suitable organic base such as pyridine or triethylamine. If the reaction does not smoothly proceed, 4-dimethylaminopyridine may be added. The reaction is carried out at a temerature ranging from room temperature to 110° C. for 0.5 to 2 hr with continuous stirring. After the reaction the reaction liquid is poured into a large quantity of water to precipitate the reaction product, and the precipitate is collected by filtration, washed with water and dried.

Acetylated methyl-calixarene (I) is well soluble in various organic solvents as described hereinbefore Although the compound (I) is an oligomer relatively low in molecular weight, we have found that this compound can be formed into a film on a substrate by a spin coating method which is usually employed for forming films of high polymers. A solution of the compound (I) suitable for use in a conventional spin coating method can easily be prepared. After forming a film of the solution on a suitable substrate the film is solidified by simple drying for example, at about 100° C. to completely dissipate the solvent. The solidified film is hard and highly heat-resistant.

A solidified film of acetylated methyl-calixarene can be dissolved in an organic solvent as explained hereinbefore. However, it is possible to three-dimensionally polymerize and insolubilize this film by exposure to a high-energy ray such as ion beam, electron beam or X-ray. If a known photosensitive bifunctional cross-linking agent is added to the solution for forming the film it is possible to accomplish cross-linked polymerization of the solidified film by exposure to actinic light.

By using the solubilities and polymerizability of acetylated methyl-calixarene (I), it is possible to form a fine pattern in a film of this compound formed on a suitable substrate. A fundamentally known pattern-forming method is used. First, the film is selectively irradiated with a high-energy ray for polymerization of the calixarene in the desired regions of the film. Next, the film is treated with a suitable organic solvent to dissolve the calixarene in the unirradiated regions. The polymerized regions remain undissolved, so that a pattern of negative type is formed. The organic solvent for the developing treatment may be a good solvent for acetylated methyl-calixarene such as the one used in preparing the solution of the calixarene. However, it suffices to use a poor solvent for the calixarene, such as an alcohol, as the developing solvent because a relatively large quantity of the solvent is used for this purpose. If a good solvent is used there is a possibility of degrading the obtained pattern, for example, in respect of rectangularity.

EXAMPLE 1

Synthesis

First 18.7 g of p-methylphenol was dissolved in 150 ml of xylene, and 9 g of paraformaldehyde was added to the solution, followed by the addition of 0.4 ml of 10 N aqueous solution of potassium hydroxide. The resultant mixture was heated under reflux for 4 hr, and then a precipitated reaction product was separated from the reaction liquid by filtration, washed first with acetone and then with ethanol and dried. The dried product was further washed with a mixture of ethanol and water and dried. The dried product was 10.3 g of methyl-calixarene.

Figure 2:
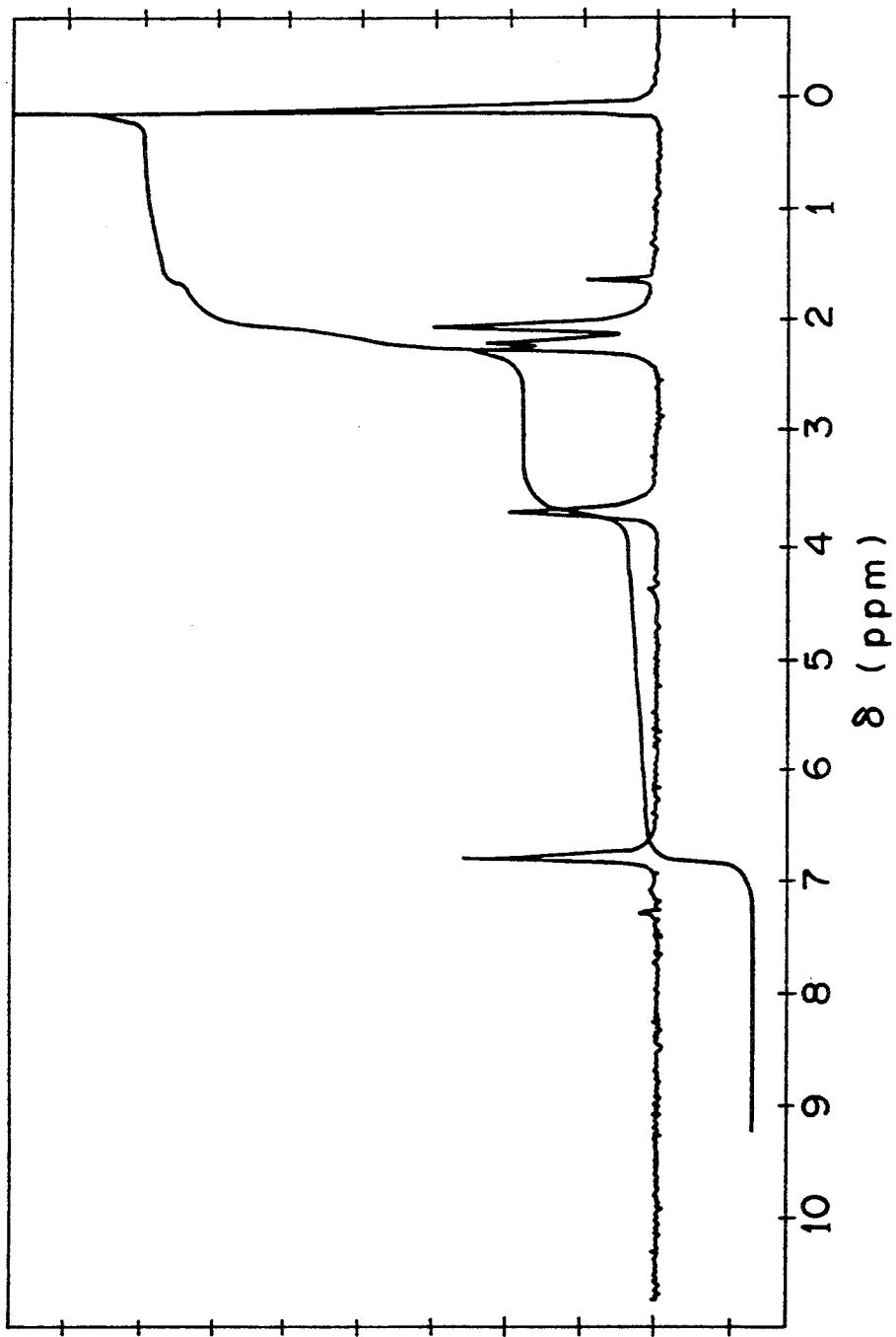
FIG. 2 is a proton NMR spectrum chart of acetylated methyl-calix[6]arene.

Next, 3.0 g of methyl-calixarene was dissolved in 30 ml of pyridine, and 1 ml of acetic anhydride was added. The thus prepared reaction liquid was stirred for 30 min at room temperature. After that the reaction liquid was poured into 300 ml of water, and a white precipitate was separated from the liquid by filtration, washed with water and dried. The dried product was 3.7 g of acetylated methyl-calixarene. From the IR absorption spectrum chart shown in FIG. 1, NMR spectrum chart shown in FIG. 2 and mass spectrum data (972) the finally obtained product was identified as fully acetylated methyl-calix[6]arene, viz. 5,11,17,23,29,35-hexamethyl-37,38,39,40,41,42-hexaacetoxycalix[6]arene.

A solution of this compound in acetone was vigorously stirred for several minutes to result in the appearance of a white precipitate. The precipitate was recovered and dried. This precipitate was an isomer of the initially dissolved acetylated methyl-calix[6]arene, but the isomerization produced no change in the IR, NMR and mass spectrum data.

EXAMPLE 2

Film Formation

Acetylated methyl-calix[6]arene was dissolved in toluene to obtain a 10 wt % solution, and the solution was passed through a filter having 0.2 μm openings. Then the solution was applied to a silicon substrate by a spin coating method, which was performed initially at 300 rpm for 5 sec and thereafter at 1500 rpm for 60 sec. The coated substrate was heated in nitrogen gas at 100° C. for 30 min. As the result, a uniformly hard film having a thickness of about 0.45 μm was formed on the substrate.

EXAMPLE 3

Pattern Formation

The film formed Example 2 was selectively irradiated with an ion beam by using a focusing ion-beam lithography apparatus to polymerize the film material in the irradiated regions The ion was $Be^{++}$; acceleration energy was 260 KeV; beam current was 9.6 pA; beam diameter was about 0.1 μm; exposure dose was $4.0 \times 10^{13}$ ions/cm$^2$. Then the film was dipped in ethanol for 30 min to dissolve and remove the unirradiated regions. After that the remaining portion of the film was baked at 80° C. for 30 min.

By observation with SEM. the obtained pattern was very good in rectangularity and very accurate even in areas where the line width was 0.1 μm. To test heat resistance the pattern was heated at 300° C. for 30 min, but there was no change in the shape of the pattern elements.

The pattern-forming process was modified by alternately using electron beam and X-ray in place of the ion beam, and similarly good results were obtained in both cases.

Compared with acetylated methyl-calixarene, known calixarenes and calixarene derivatives are far inferior in solubilities in various organic solvents Nevertheless, we have tried to form films of calixarenes and calixarene derivatives represented by the general formula (II) from their dilute solutions by spin coating and, unexpectedly, have discovered that films thicker than 10 nm can be formed on various substrates by spin coating if the solvent and the spin coating conditions are suitably chosen. Films thinner than 10 nm are liable to have defects and hence may not be suitable for practical uses.

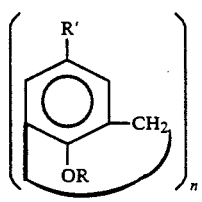

(II)

where R is —H, —CH$_3$, —COCH$_3$, —(CH$_2$)$_m$CH$_3$, where m is an integer from 1 to 9, —CH$_2$CHCH$_2$, —SiCH$_3$, CH$_2$COOH, —COAr or —CH$_2$Ar, where Ar represents aryl group, R' is —H, an alkyl group having 2 to 10 carbon atoms, aryl group, —Br, —SO$_3$Na, —CH$_2$NH$_2$, CH$_2$Cl, —NO$_2$, —N=NAr, —COAr or —ArCOCH=CH$_2$, where Ar represents aryl group, and n is an integer from 4 to 8.

In general it is desirable to use an organic solvent which has a relatively high boiling point and is good in the ability to wet the employed substrate. For example, pyridine is favorable in respect of solubilities but is not favorable for application to glass, quartz or silicon substrates. In most cases cyclohexanone and dioxane are preferable solvents.

After applying a dilute solution of a selected calixarene or its derivative to a substrate by a spin coating method, the coated substrate is baked at a temperature not higher than 400° C., that is, a temperature at which the film material is still stable. The obtained film is high in heat resistance and has a high hardness compared with films of popular polymers.

EXAMPLE 4 tert-Butyl-calix[8]arene was prepared by the reaction of p-tert-butylphenol with paraformaldehyde in xylene in the presence of potassium hydroxide. After refining by recrystallization the product had a melting point of 411°–412° C.

Th obtained tert-butyl-calix[8]arene was dissolved in cyclohexanone to prepare a 0.25 wt % solution, and the solution was passed through a filter with 0.2 μm openings. The solution was applied to a silicon substrate by spin coating, which was performed initially at 300 rpm for 10 sec and thereafter at 800 rpm for 60 sec. The coated substrate was baked at 150° C. for 30 min. The solidified film was hard and had a thickness of about 60 nm.

EXAMPLE 5

The following calixarenes were tested.

(1) tert-Butyl-calix[4]arene

This compound was prepared by the reaction of p-tert-butylphenol with aqueous solution of formaldehyde in the presence of sodium hydroxide. After refining by recrystallization the product had a melting point of 344°–346° C.

(2) tert-Octyl-calix[8]arene

This compound was prepared by the reaction of p-tert-octylphenol with paraformaldehyde in xylene in the presence of potassium hydroxide. After refining by recrystallization the product had a melting point of 338°–340° C.

(3) Calix[6]arene

This compound was prepared by the reaction of tert-butyl-calix[6]arene with phenol in xylene in the presence of aluminum chloride. After refining the product had a melting point of 380°–381° C.

(4) Acetylated t-butyl-calix[8]arene

This compound was prepared by the reaction of t-butyl-calix[8]arene with acetic anhydride in pyridine.

In the cases of the known calixarenes (1) to (4) the solubilities in organic solvents, including cyclohexanone, were below 0.25 wt %. However, it was possible to form thin films from dilute solutions of these calixarenes by the same spin coating method as in Example 4, and in every case a hard film having a thickness of about 60 nm was formed on the silicon substrate. Supplementarily, a 1:1 mixture of the solution used in Example 4 and the solution of the compound (3) was used in the same film-forming process, and a similar resut was obtained.

Among known calixarenes and their derivatives, acetylated tert-butyl-calix[6]arene exhibits good solubilities in organic solvents. It was possible to prepare 10 wt % solution of tert-butyl-calix[6]arene in a suitable solvent such as cyclohexanone, but the heat resistance of the film formed from the solution was below 200° C.

What is claimed is:

1. A film of acetylated methyl-calix[n]arene represented by the formula (I):

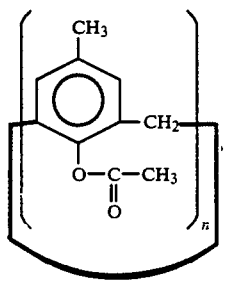

where n is an integer from 4 to 8, the film being thicker than 10 nm and formed from a solution of said acetylated methyl-calix[n]arene in an organic solvent by applying said solution directly to a substrate and thereafter removing said solvent.

2. A film according to claim 1, wherein n in the formula (I) is 6.

3. A method of forming a pattern, comprising the steps of:
   (a) forming a film of acetylated methyl-calix[n]arene represented by the formula (I) thicker than 10 nm on a substrate from a solution of said acetylated methyl-calix[n]arene by applying said solution directly to a substrate and thereafter removing said solvent;
   (b) selectively irradiating said film with a high-energy ray thereby to insolubilize the irradiated regions of said film; and
   (c) removing the unirradiated regions of said film by dissolving in an organic solvent;

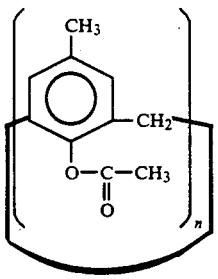

where n is an integer from 4 to 8.

4. A method according to claim 3, wherein n in the formula (I) is 6.

5. A method according to claim 3, wherein said high-energy ray is an ion beam.

6. A method according to claim 3, wherein said high-energy ray is an electron beam.

7. A method according to claim 3, wherein said high-energy ray is X-ray.

8. A method of forming a film of acetylated methyl-calix[n]arene represented by the formula (I) thicker than 10nm,

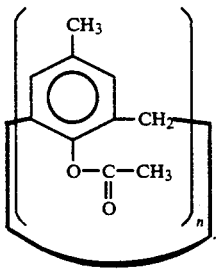

where n is an integer from 4 to 8, comprising the steps of: applying a solution of said acetylated methyl-calix[n]arene in an organic solvent directly to a substrate to thereby form a liquid film on the substrate and removing said solvent from said liquid film.

9. A method according to claim 8, wherein said solvent is applied to said substrate by spin coating.

10. A method according to claim 8, wherein n in the formula (I) is 6.

* * * * *